(12) United States Patent
Park et al.

(10) Patent No.: US 6,184,976 B1
(45) Date of Patent: Feb. 6, 2001

(54) APPARATUS AND METHOD FOR MEASURING AN AERIAL IMAGE USING TRANSMITTED LIGHT AND REFLECTED LIGHT

(75) Inventors: Jin-hong Park, Seoul; Young-hun Yu, Yongin, both of (KR)

(73) Assignee: Samsung Electronics Co., Ltd., Suwon (KR)

( * ) Notice: Under 35 U.S.C. 154(b), the term of this patent shall be extended for 0 days.

(21) Appl. No.: 08/948,057

(22) Filed: Oct. 9, 1997

(30) Foreign Application Priority Data

Oct. 10, 1996 (KR) .................................................. 96-45127

(51) Int. Cl.[7] .................................................. G01N 21/00
(52) U.S. Cl. ..................................... 356/237.4; 356/237.5; 356/239.3; 356/239.7; 356/239.8
(58) Field of Search .............................. 356/237.4, 237.5, 356/239.3, 239.7, 239.8, 237.1; 250/372

(56) References Cited

U.S. PATENT DOCUMENTS 5,098,191 * 3/1992 Noguchi et al. ..................... 356/394
5,235,400 * 8/1993 Terasawa et al. ..................... 356/394
5,737,072 * 4/1998 Emery et al. ........................... 356/73
5,892,579 * 4/1999 Elyasaf et al. .................... 356/239.8

* cited by examiner

Primary Examiner—Frank G. Font
Assistant Examiner—Amanda Merlino
(74) Attorney, Agent, or Firm—Jones Volentine, L.L.C.

(57) ABSTRACT

Apparatus and method for measuring an aerial image whereby influences of various defects existing on patterns formed on a photomask as well as the surface of the photomask substrate can be inspected. The aerial image measuring apparatus includes an optical transmitting device, an optical reflecting device and an aerial image forming device. The optical reflecting device includes a beam splitter and a reflecting mirror. The reflecting mirror switches the path of light so that the light transmitted along the reflected light path is irradiated to the surface of the photomask on which the patterns are formed. According to an aerial image measuring method of the present invention, either transmitted light or reflected light is selected for analysis, the selected light is converted into an electrical signal to form an aerial image, and the aerial image is measured.

9 Claims, 3 Drawing Sheets

APPARATUS AND METHOD FOR MEASURING AN AERIAL IMAGE USING TRANSMITTED LIGHT AND REFLECTED LIGHT

BACKGROUND OF THE INVENTION

1. Field of the Invention

The present invention relates to an apparatus and method for fabricating semiconductors, and more particularly, to an apparatus and method for measuring an aerial image from which the effects or influences of various defects on a photomask can be inspected.

2. Description of the Related Art

In general, an aerial image that is obtained from a photomask or a reticle (hereinafter commonly referred to as "photomask") is measured in order to inspect all types of defects exhibited on the photomask to determine the resulting influence of these defects on a pattern formed on the wafers using the photomask.

FIG. 1 is a schematic view of the configuration of a conventional aerial image measuring apparatus. The conventional apparatus for measuring an aerial image includes an optical source 2 for emitting light, e.g., deep ultraviolet (DUV) or I-line, a motor filter 4 having a filter suitable for a wavelength of light irradiated from the optical source 2, and a condenser lens 10 for condensing light that passed through an illumination aperture 6 and a vision aperture 8. The illumination aperture 6 controls the numerical aperture (NA) and the coherency of the light. The condensed light is then emitted to a surface of a photomask 50 opposite to the surface on which a chrome pattern 52 is formed.

A charge-coupled device (CCD) camera 30 forms an aerial image by converting light passing through the photomask 50 into an electrical signal. An aerial image measurement system (AIMS) 40 measures the aerial image. The light passing through the photomask 50 is transmitted to the CCD camera 30 via an objective lens 12, a tube lens 14, a 7×expanded projection lens 16 and an imaging aperture 20. An auxiliary lens 22 for observing the numerical aperture (NA) and the coherency is installed between the imaging aperture 20 and the CCD camera 30. Also, a CCD camera 15 for visible ray observation is installed to observe light focused on the tube lens 14 through the objective lens 12 using an auxiliary outputter (not shown) such as a monitor.

In the conventional aerial image measuring apparatus having such a configuration, light from the optical source 2 is irradiated to the surface of the photomask 50 opposite to the surface on which the chrome pattern 52 is formed so that an aerial image is measured using only the light passing through the photomask.

As a result, the conventional aerial image measuring apparatus can not inspect all types of defects which may exist on the photomask pattern so that the effects or influences of such defects on the photomask can not be accurately determined.

More specifically, the conventional aerial image measuring apparatus measures only an aerial image formed by the light passing through the photomask from the surface of the photomask opposite to the surface on which the chrome pattern is formed. Therefore, one cannot inspect the effects of numerous factors existing over the entire upper surface of the photomask on which the chrome pattern is formed. Such effects that should be inspected include: the reflectivity variation on the surface of an anti-reflection layer coated on the chrome pattern; chrome particles remaining at a repaired portion or its adjacent portion after a defect on the photomask is repaired; an ion beam source, e.g., gallium, in case that the chrome is removed by an ion beam; a damaged portion on the photomask generated after the defect on the photomask is repaired; the thickness variation of the chrome pattern layers formed on the photomask; and contaminants, such as flowable or unflowable particles existing on the chrome pattern formed on the photomask, or other organic materials generated during various processes.

SUMMARY OF THE INVENTION

It is an object of the present invention to provide an aerial image measuring apparatus which can inspect various defects existing on the patterns formed on a photomask as well as on the surface of the substrate of the photomask.

It is another object of the present invention to provide an aerial image measuring method which can inspect various defects existing on the patterns formed on a photomask as well as on the surface of the substrate of the photomask.

To achieve these and other advantages, the present invention provides for an aerial image measuring apparatus that inspects defects on the photomask on which predetermined patterns are formed by using an aerial image formed by light passing through a photomask from an optical source. The apparatus according to the present invention includes an optical transmitting section for irradiating light from the optical source to a photomask and forming a transmitted light passing through the photomask. Also, an optical reflecting section irradiates the light from the optical source to the surface of the photomask on which patterns are formed and forms a reflected light reflected by the surface on which the patterns are formed. An aerial image forming device forms an aerial image by converting one of the transmitted light and the reflected light into an electrical signal.

The optical reflecting section includes a beam splitter for splitting the light emitted from the optical source into a transmitted light path along which the transmitted light is advanced and a reflected light path along which the reflected light is advanced, and a reflecting mirror for altering a light path so that the light transmitted along the reflected light path is irradiated to the surface of the photomask on which the patterns are formed.

An on/off device, respectively installed in the transmitted light path and the reflected light path, selectively blocks or passes the light transmitted to each of the transmitted light path and the reflected light path.

The aerial image measuring apparatus according to another embodiment of the present invention inspects defects on a photomask on which predetermined patterns are formed, using an aerial image formed by light emitted from first and second optical sources and passing through the photomask. The apparatus includes an optical transmitting section for irradiating the light emitted from the first optical source to the photomask and forming transmitted light passing through the photomask. An optical reflecting section irradiates the light emitted form the second optical source to the surface of the photomask on which the patterns are formed and forms reflected light reflected from the surface on which the patterns are formed. An aerial image forming device forms an aerial image by converting one of the transmitted light and the reflected light into an electrical signal.

The optical reflecting section includes a reflecting mirror for altering the path of light to irradiate the light emitted from the second optical source to the surface of the photomask on which the pattern is formed.

In another aspect, the present invention provides for a method of measuring an aerial image comprising the steps of providing light emitted from an optical source to a lower surface of the photomask and forming transmitted light passing through the photomask; providing the light emitted from the optical source to the upper surface of the photomask and forming reflected light reflected from the upper surface on which the patterns are formed; selecting one of the transmitted light and the reflected light for analysis; converting the selected light into an electrical signal to form an aerial image; and measuring the aerial image.

According to the present invention, aerial images of the photomask based on the transmitted light as well as the reflected light can be measured. Therefore, the effects or influences of every type of defect on the photomask can be accurately inspected.

BRIEF DESCRIPTION OF THE DRAWINGS

The above objects and advantages of the present invention will be described with reference to the accompanying drawings, in which.

DETAILED DESCRIPTION OF PREFERRED EMBODIMENTS

Figure 1:
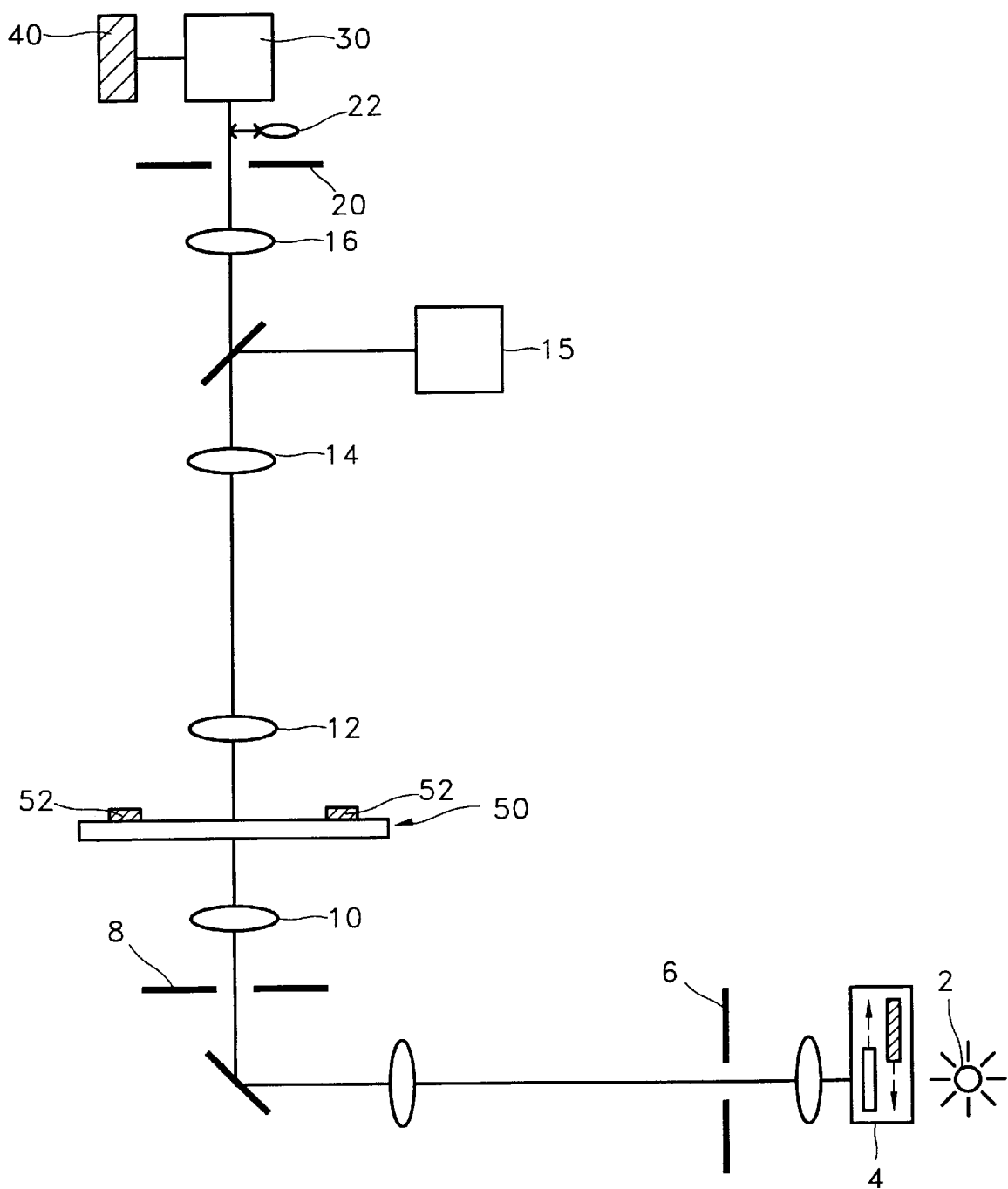
FIG. 1 is a schematic view showing the configuration of a conventional apparatus for measuring an aerial image.
Figure 2:
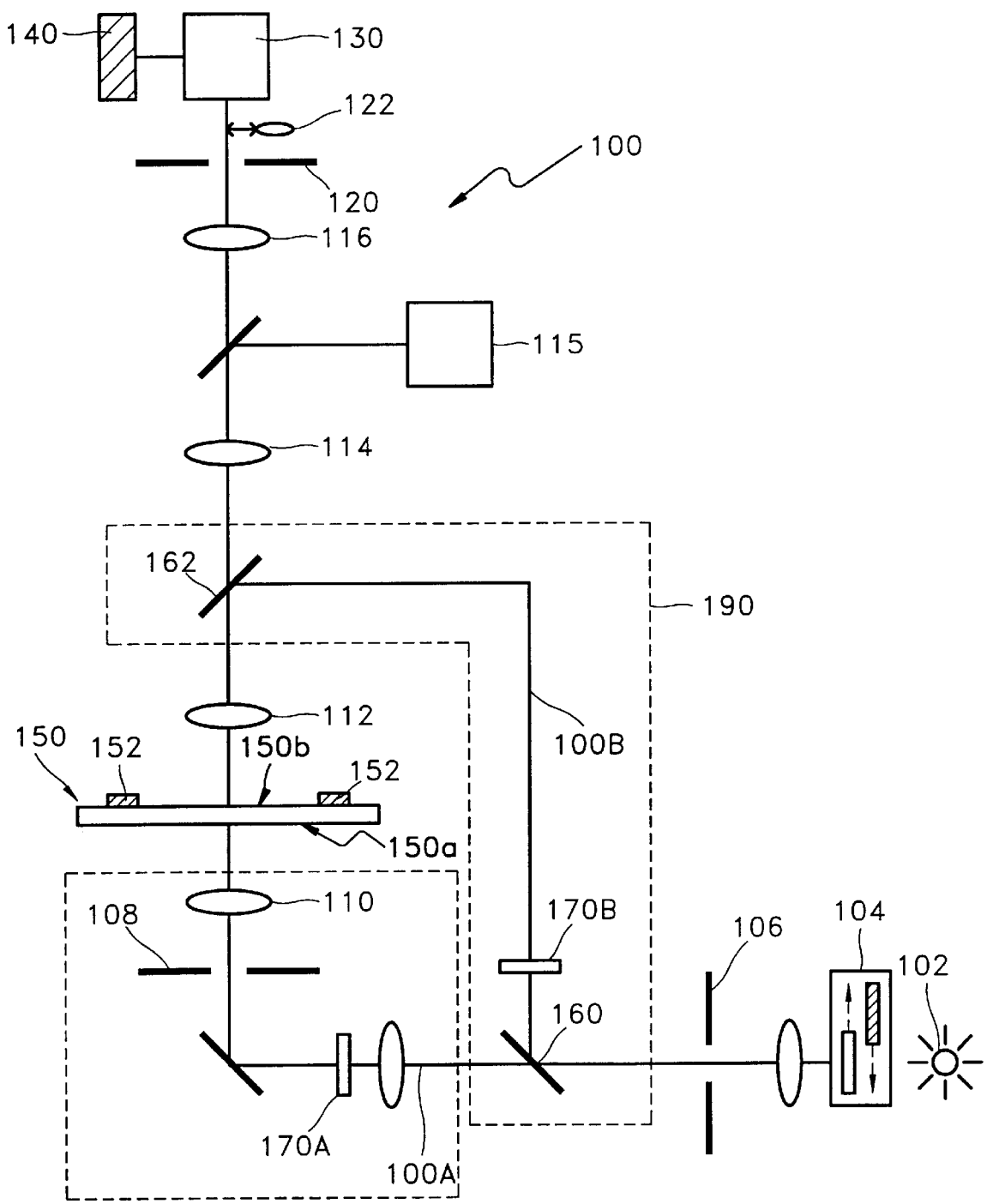
FIG. 2 is a schematic view showing the configuration of an apparatus for measuring an aerial image according to an embodiment of the present invention.

Referring to FIG. 2, an aerial image measuring apparatus 100 according to a preferred embodiment of the present invention includes an optical transmitting section 180. The optical transmitting section 180 irradiates light emitted from an optical source 102 to a lower surface 150a of a photomask 150 and forms a transmitted light passing through the photomask 150. Defects on the photomask 150 are inspected using an aerial image formed by the light passing through the photomask 150 from the optical source 102.

An optical reflecting section 190 irradiates the light emitted from the optical source 102 to an upper surface 150b of the photomask 150, on which chrome patterns 152 are formed, and forms a reflected light that is reflected by the surface 150b on which the chrome patterns 152 are formed.

A CCD camera 130 forms an aerial image by converting a light selected from the transmitted light and the reflected light into an electrical signal.

The optical reflecting section 190 is comprised of a beam splitter 160 for splitting the light emitted from the optical source 102 into a transmitted light path 100A along which the transmitted light is advanced, and a reflected light path 100B along which the reflected light is advanced. A reflecting mirror 162 switches or alters the path of light so that the light advanced along the reflected light path 100B is irradiated to the surface 150b of the photomask 150 on which the chrome patterns 152 are formed.

Also, on/off means, e.g., on/off blinkers 170A and 170B, selectively block or pass light advanced to the transmitted light path 100A and the reflected light path 100B. The on/off blinkers 170A and 170B are installed along the transmitted light path 100A in the optical transmitting section 180 and the reflected light path 100B in the optical reflecting section 190, respectively. Accordingly, the light advanced to the transmitted light path 100A and the reflected light path 100B are blocked or passed according to an "on" or "off" state of the on/off blinkers 170A and 170B. Therefore, an aerial image using the transmitted light or an aerial image using the reflected light can be selectively formed.

For example, in the optical transmitting section 180, when the on/off blinker 170A is "on", light passing through the on/off blinker 170A from the optical source 102 passes through a vision aperture 108, proceeds via a condenser lens 110 to the surface 150a of the photomask 150 opposite to the surface 150b on which the chrome patterns 152 are formed, and then passes through the photomask 150.

The aerial image measuring apparatus 100 includes a DUV or I-line optical source 102. As in the conventional apparatus, a motor filter 104 having a filter suitable for a wavelength of light irradiated from the optical source 102, and an illumination aperture 106 for controlling the NA and the coherency of the light, are installed between the optical source 102 and the beam splitter 160.

The condenser lens 110 is installed in the transmitted light path 100A for condensing light passing through the vision aperture 108 and transmitting the light to the surface 150a of the photomask 150 opposite to the surface 150b on which the chrome pattens 152 are formed. The light advanced along the reflected light path 100B is irradiated to the surface 150b of the photomask 150 on which the chrome patterns 152 are formed by the reflecting mirror 162. The reflected light of light irradiated on the photomask 150 along the reflected light path 100B in the optical reflecting section 190, and the transmitted light passing through the photomask 150 along the transmitted light path 100A in the optical transmitting section 180, are transmitted to a CCD camera 130 and an aerial image measurement system (AIMS) 140 via an objective lens 112, a tube lens 114, a 7×expanded projecting leans 116 and an upper aperture 120.

In the CCD camera 130, therefore, the transmitted light passing through the photomask 150 along the transmitted light path 100A, or the reflected light reflected by the surface 150b of the photomask 150 along the reflected light path 100B are converted into an electrical signal to form an aerial image. The AIMS 140 exhibits the state of the defected photomask 150 using the aerial image as formed above.

An auxiliary lens 122 for observing the NA and the coherency of the light is installed between the upper aperture 120 and the CCD camera 130. Also, a CCD camera 115 for visible ray observation can be installed to observe light focused on the tube lens 114 using an auxiliary outputter (not shown) such as a monitor.

Figure 3:
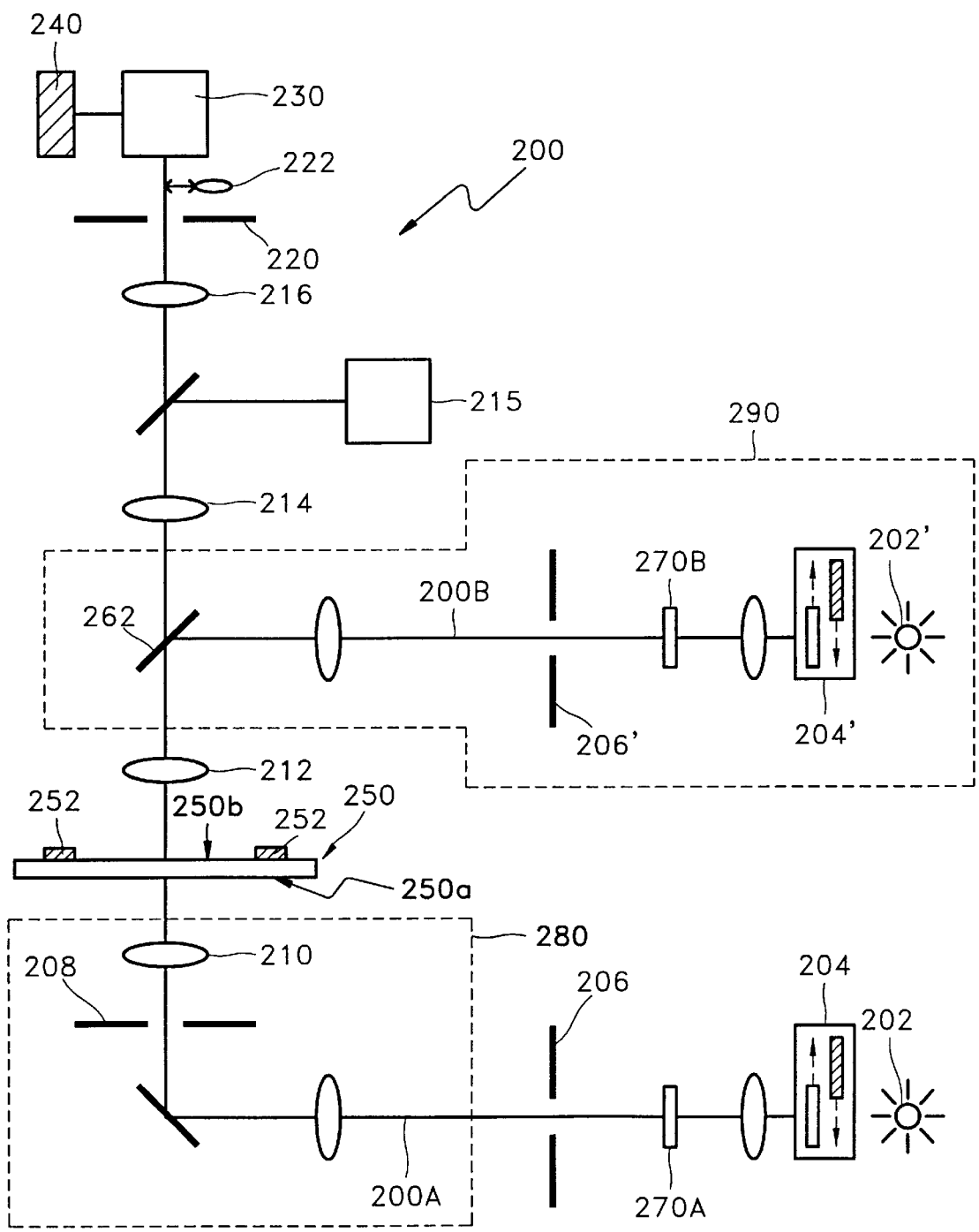
FIG. 3 is a schematic view showing the configuration of an apparatus for measuring an aerial image according to another embodiment of the present invention.

FIG. 3 is a schematic view showing the configuration of an aerial image measuring apparatus according to another embodiment of the present invention.

The embodiment of FIG. 3 is somewhat similar to the embodiment described with reference to FIG. 2. The similar members in FIG. 3 are indicated by 200-series reference numerals corresponding to the 100-series reference numerals of FIG. 2 and therefore will not be described in detail.

In the aerial image measuring apparatus according to another embodiment of the present invention as shown in FIG. 3, the optical reflecting section 290 uses an additional separately installed optical source 202' for forming an aerial image on the basis of a reflected light reflected by the surface 250b of the photomask 250 on which chrome patterns 252 are formed. Light emitted from the additional optical source 202' is irradiated to the surface 250b of the photomask 250 on which the chrome pasterns 252 are formed. Therefore, the beam splitter 160 of FIG. 2 is not necessary in the embodiment of FIG. 3. The on/off blinker 270B selectively blocks or passes the light transmitted from the additional optical source 202' to a reflected light path 200B. An illumination aperture 206' is installed between the additional optical source 202' and a reflecting mirror 262 for controlling the NA and the coherency of the light.

According to the following method, the aerial image measuring apparatus of the present invention inspects defects existing on the photomask on which predetermined patterns are formed based on an aerial image that is formed from light emitted from at least one optical path that passes through, or is reflected by, the photomask.

In a selection step, either transmitted light passing through a photomask by light emitted from a first optical path is irradiated to the photomask, or reflected light reflected by the photomask by light emitted from a second optical path is irradiated to the surface of the photomask on which patterns are formed, is selected.

The selected light is then converted into an electrical signal to form an aerial image. The aerial image is thereafter measured to inspect the effects or influences of various defects existing on the photomask on wafers.

The first and second optical paths may generated by a single optical source, as in the embodiment of FIG. 2, or by different optical sources, as in the embodiment of FIG. 3. Either a DUV or I-line optical source can be used.

As described above, according to the preferred embodiment of the present invention, aerial images of the photomask based on the transmitted light as well as the reflected light can be measured to inspect influences of various defects existing on the photomask. Therefore, influences of every type of defect on the photomask can be accurately inspected, and the allowable level of defects on the photomask can be easily determined.

Although the present invention is described in detail referring to a preferred embodiments, it is not limited to the disclosed embodiments. It is apparent that various modifications may be effected by those skilled in the art within the technical spirit of the present invention.

What is claimed is:

1. An aerial image measuring apparatus for inspecting effects of defects on a photomask on which predetermined patterns are formed on an upper surface thereof, the apparatus comprising:

an optical transmitting section for irradiating light emitted from an optical source to a lower surface of the photomask and forming transmitted light passing through the photomask;

an optical reflecting section for irradiating the light emitted from the optical source to the upper surface of the photomask and forming reflected light reflected from the upper surface on which the patterns are formed. the optical reflecting section comprising:

a beam splitter for splitting the light emitted from the optical source into a transmitted light path along which the transmitted light is advanced and a reflected light path along which the reflected light is advanced, and a reflecting mirror, installed in the reflected light path between the optical source and the upper surface of the photomask, for altering the reflected light path to irradiate the reflected light to the upper surface of the photomask on which the patterns are formed; and an aerial image forming device for forming an aerial image by converting one of the transmitted light and the reflected light into an electrical signal.

2. The apparatus of claim 1, further comprising:

an on/off device installed along the transmitted light path between the optical source and the lower surface of the photomask for selectively blocking or passing the transmitted light advanced along the transmitted light path; and another on/off device installed along the reflected light path between the optical source and the reflecting mirror for selectively blocking or passing the reflected light advanced along the reflected light path.

3. The apparatus of claim 2, further comprising an aperture installed between the optical source and the beam splitter for controlling a numerical aperture and a coherency of the light emitted from the optical source.

4. The apparatus of claim 3, wherein the optical source is a deep ultraviolet (DUV) or I-line optical source.

5. A method of measuring an aerial image to inspect effects of defects on the photomask on which a predetermined pattern is formed on an upper surface thereof, the method comprising:

(a) providing light emitted from a first optical path to a lower surface of the photomask and forming transmitted light passing through the photomask;

(b) providing light emitted from a second optical path to the upper surface of the photomask and forming reflected light reflected from the upper surface on which the patterns are formed;

(c) selecting one of the transmitted light and the reflected light for analysis;

(d) converting the selected light into an electrical signal to form an aerial image; and (e) measuring the aerial image, wherein the first optical path and the second optical path are generated by a single light source during the providing steps (a) and (b).

6. The method of claim 5, further comprising a step of splitting said single light source into the first optical path and the second optical path during said providing steps (a) and (b).

7. The method of claim 5, wherein the first optical path and the second optical path are respectively generated by two separate light sources during the providing steps (a) and (b).

8. The method of claim 5, said selecting step (c) including a step of selectively blocking one of the transmitted light and the reflected light.

9. The method of claim 5, wherein a DUV or I-line optical source is used as the optical source.

* * * * *